United States Patent [19]

Cohen

[11] Patent Number: 4,602,004
[45] Date of Patent: Jul. 22, 1986

[54] ALOIN AND ALOE-EMODIN CONTAINING PESTICIDES

[76] Inventor: Maurice Cohen, Caracas, Venezuela

[21] Appl. No.: 620,506

[22] Filed: Jun. 14, 1984

[51] Int. Cl.$^4$ .................. A61K 31/70; A61K 31/12
[52] U.S. Cl. .................................. 514/23; 260/365; 514/680; 536/1.1
[58] Field of Search .................. 536/1.1; 260/365; 514/23, 680

[56] References Cited

U.S. PATENT DOCUMENTS 4,215,062  7/1980  Mitscher ........................ 260/365

OTHER PUBLICATIONS

Lemli et al., vol. 90, 1979, "Chem. Abst.", p. 76458(j).
Gruen et al., "Chem. Abst.", vol. 96, 1982, p. 139751(w).
Hokkai Sankyo Co., "Chem. Abst.", vol. 101, 1984, p. 165598(t).

Primary Examiner—Johnnie R. Brown
Attorney, Agent, or Firm—Cushman, Darby & Cushman

[57] ABSTRACT

Invertebrate pests including arthropods, annelids, and vermids are substantially completely killed upon contact with a compound selected from the class consisting of

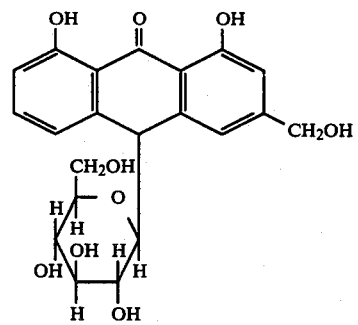

and

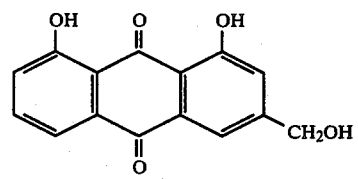

Both members of the class may be extracted from plants of the aloe genus.

9 Claims, No Drawings

ALOIN AND ALOE-EMODIN CONTAINING PESTICIDES

FIELD OF THE INVENTION

This invention relates to broad spectrum pesticide formulations, and in particular to methods of exterminating agricultural, garden, veterinary, etc. invertebrate pests using compounds which occur naturally.

BACKGROUND OF THE INVENTION

Much time and expense has been devoted to developing pesticides which together are efficacious for killing a broad spectrum of agricultural, garden, and veterinary pests. Compounds and compositions have been developed for combatting numerous invertebrate pest varieties, for example, in situations ranging from ridding domestic pets of fleas to protecting vast acreages of staple crops from the depredations of numerous species of insects.

For example, active pesticide (e.g. insecticide) ingredients have been developed that are extremely efficacious, including arsenicals, fluorides, dinitrophenols, organothiocyanates, and numerous highly halogenated compounds, to name but a few. See generally Kirk Othmer, *Encyclopedia of Chemical Technology*, Volume 13, Wiley-Interscience, Third Edition.

Several drawbacks to the use of synthetic pesticides do exist, however, and these stem principally from these substances' deleterious effects, both immediate and long range, on the environment. That is, many synthetic pesticides are extremely persistent (i.e. do not biodegrade easily) and build up high residue levels as repeated seasonal applications are made. Concern arises not only from ecological implications inasmuch as, for example, some insecticides (e.g., parathion) are known to be lethal to animals, but also from other obvious concerns stemming from the dangers of contaminating human food and water supplies inasmuch as many pesticides are known to be toxic to humans in varying degrees depending at least in part, of course, on the levels of pesticide present.

Against this background what is needed is an efficacious pesticide which does not impart persistent residues to the environment and which, at reasonable application levels, is non-toxic to man and animals. Any compound having this highly desirable combination of properties would be particularly useful if, in addition, it exhibited broad spectrum activity (i.e., against as wide a range of invertebrate pests as possible), was easily obtainable, and was cheap to produce. Such active pesticide ingredients are the subject of this invention.

Insecticides which include plant extracts or plant-based ingredients are known, for example, from U.S. Pat. Nos. 4,361,554 to Saunders and 287,701 to Miller. Neither of these patents discloses any specific insecticidal ingredient, however, both alluding only to "extracts" or "infusions". The Saunders plant extract/insecticide is stated to be effective only against insects lacking an exoskeleton. The Miller patent discloses a multi-component composition which includes plant-based ingredients disclosed in very general fashion. Neither patent discloses the specific ingredients disclosed herein or the plant source from which they may be obtained.

SUMMARY OF THE INVENTION

This invention makes possible the extermination of virtually all types of invertebrate pests which are members of the animal kingdom phyla arthropoda and annelida by exposing the pests to at least one of two compounds each of which occurs naturally in species of aloe plants (family - Liliaceae), such as aloe vera. The first compound is commonly known as aloin and has the structure:

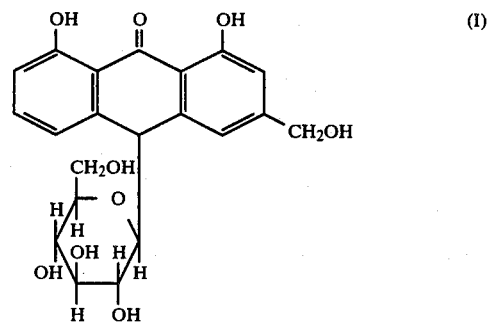

The second compound is commonly known as aloe-emodin and is essentially (I) without the glucose moiety, having the following structure:

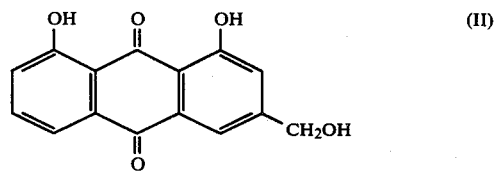

It has been determined that the above compounds (I) and (II) are lethal to virtually all types of invertebrate pests regardless of whether the particular pest species possesses an exoskeleton or not. The compounds are effective against virtually all arthropods, including members of the following classes:

Arachnida (e.g. spiders, scorpions, ticks)
Insecta (e.g. cockroaches, crickets, beetles, flies, locusts, etc.)
Merostomata
Myriapoda Additionally, the compounds (I) and (II) show effectiveness against non-arthropod pests as well, for example worms in general (e.g. earthworms, leeches) such as those members of the phylum Annelida.

Advantageously, at levels efficacious for eliminating invertebrate pests, both aloin and aloe-emodin are non-toxic to plants and animals, and both also possess effectiveness lasting anywhere from several days to several weeks, depending in part on the level applied. Further, both compounds are biodegradable such that persistent residues contaminating the environment are not a problem.

Compounds (I) and (II) can also be used in preventive compositions to deter or prevent infestation or reinfestation by pests. If it is desired to rid e.g. a household pet of fleas, the animal may first be shampooed with a shampoo composition containing aloin or aloe-emodin to kill the existing flea population. Then, an additional application of a repellant or preventive composition containing aloin or aloe-emodin can be made to prevent fleas from reestablishing a population.

DETAILED DESCRIPTION

The formulations of this invention contain an amount of aloin or aloe-emodin effective to rid a host (be it animal or plant, or even the ground itself) of substantially all invertebrate pests located thereon (or therein if it is ground treatment which is contemplated). The formulations are applied topically, as opposed to internally, and may take any form desired depending on the application—shampoos, creams, lotions, sprays, aqueous solutions, etc.

Although aloin and/or aloe-emodin are the active ingredients in the formulations of this invention, other ingredients which do not affect the activity may also be included. Such other ingredients include, but are not limited to, antioxidants (e.g. potassium sorbate), surfactants, dry insect food/attractants (e.g., for use in an insect trap using aloin), perfumes or deodorants, etc.

The formulation may be emulsified, dispersed or dissolved in a suitable carrier or solvent which may again depend on the application. For example, aloin or aloe-emodin may be dissolved in an agriculturally aceptable carrier such as water with a suitable antioxidant for application to crops, both compounds being reasonably soluble in water. For a different application such as in a commercial preparation for application in the home to combat e.g. cockroaches or spiders, dissolution in a solvent such as kerosene would be more appropriate.

Aloin may be prepared by direct extraction directly from aloe plants (class—monocotyledeae, family—Liliaceae), a large genus of succulent plants of the lily family found growing, for example, in Southern Africa, South America, and in certain Caribbean islands. Different species of aloe produce extracts suitable for making the formulations of this invention, and the effectiveness of different extracts may vary slightly.

All parts of the aloe plant are usable in making the extract, but the leaves are particularly suitable for obtaining aloe juice by macerating aloe plants or parts thereof.

Aloin or aloe-emodin may be obtained depending on the manner in which the aloe juice is treated. Aloin is made by preliminarily mixing aloe juice with distilled water and then drying at about 148°–149° C. until lemon yellow crystals form. When the entire solution has been dried, only yellow aloin crystals remain.

To obtain aloe-emodin one starts by dissolving about 50 grams of ferric chloride in about 150 ml of distilled water and adding the resulting solution to about 20 grams of the aloe juice. The resulting solution is then refluxed for about 6 hours and then filtered. The refluxed solution is dried and extracted with boiling toluene. Upon cooling the toluene extract, aloe-emodin recrystallizes as orange needles. Both aloin and aloe-emodin are also obtainable commercially, for example from Aicia, Venezuela, as a crystalline product.

The recrystallized (or commercially purchased) aloin or aloe-emodin may then be added to a suitable solvent. The inventor has determined that a stock solution of active ingredient for use in making working formulations can be made by adding about 5.5 grams of the dried (crystallized) aloe juice extract to enough water or propylene glycol to make 100 milliliters. These amounts, of course, represent approximate proportions which can be varied as desired to suit the application by means of simple empirical stuides or trial runs. The amount of aloin or aloe-emodin used to make the stock solution can also vary depending on the purity of the aloin or aloe-emodin.

Using the stock aloin or aloe-emodin solution, one then formulates the insecticide by making up the final product for application to contain from about 8 to about 15% by weight of the stock solution. The exact weight percentage may vary depending, for example, on a particular arthropod to be exterminated and on the host (e.g., dog versus plant). The aloin or aloe-emodin should be present in any particular product or formulation in an amount sufficient to kill the particular invertebrate pest of interest. It is noted that it is well within the scope of this invention to vary the proportion of aloin or aloe-emodin in the final product, to formulate the insecticide starting from a different strength stock than the exemplary one cited above, or to use a different solvent. It is noted that propylene glycol has been cited as an exemplarly alternative to water in applications where a non-volatile solvent is preferred because it is nontoxic. Aloin and aloe-emodin are soluble in a wide range of other solvents as well such as hydrocarbons and alcohols.

Water is preferred as solvent.

In some formulations it may be desirable simply to add aloin or aloe-emodin directly to the ingredient mixture being worked up, i.e., without first making a stock solution.

A stock emulsion may also be used in the same manner as a stock solution using, as emulsifier, a conventional substance such as sodium lauryl sulfate (obtainable from Henkel Kommenditgesellschaft under the name Texapon N 40).

The inventor has conducted experiments using at least two species of invertebrate from each of the classes previously cited, with substantially 100% mortality rates in each case. It appears not to matter whether the species, if an arthropod, possesses a chitinous exoskeleton or not, the aloin or aloe-emodin passing through the exoskeleton and ectoderm and producing substantially immediate results. In the case of certain insects that manifest behavioral patterns of rubbing antennae or legs together (e.g. cockroaches), the killing action is particularly rapid and sudden.

The following examples are intended to serve as a representative cross-section of different modes and formulations for use in practicing the invention. They are not to be taken, however, as limiting the scope of the invention.

EXAMPLE I

Shampoo Formulation

The following is a formulation useful for human or veterinary use in combatting arthropods such as lice, fleas, and mites.

| | |
|---|---|
| Texapon N 40 (Henkel) | 25% |
| Poliquart M | 2% |
| Bronidox* | 0.2% |
| Aloin (5.5% stock solution in propylene glycol) | 10% |
| Water | 62.8% |

*Trademark of Henkel & CIE for 5-bromo-5-ntiro-1,3-dioxane.

Using the above shampoo formulation results in substantially complete elimination of the above-noted parasites for a time ranging anywhere from 7 to 8 days to 3 weeks depending on how available the parasites are for reinfestation directly from the immediate environment. No irritation of any sort was observed to occur from this shampoo.

EXAMPLE II

General Purpose Aqueous Anti-Invertebrate Formulation

| | |
|---|---|
| Aloin (5.5% aqueous stock solution in propylene glycol) | 7–10% |
| Potassium Sorbate | 0.1% |
| Water | 90–93% |

The above formulation can be used generally to treat crops or, on a smaller scale, home garden pests. It was observed that the above formulation applied to plants once a day for two days resulted in eliminating substantially all insects without damaging the plants. The above formulation may also be used in other applications such as ground application to eliminate earthworms, slugs, grubs, etc.

EXAMPLE III

Commercial Domestic Bug Killer

| | |
|---|---|
| Aloin Solution (5.5% in propylene glycol) | 7–10% |
| Quidewet Doss 50 (Humectant) | 1% |
| Kerosene or Alcohol | 90–92% |

The above formulation is effective against domestic insect infestations such as cockroaches, spiders, etc., killing virtually on contact.

EXAMPLE IV

Formulation As Repellent/Preventive Composition

| | |
|---|---|
| Aloin (5.5% stock solution in propylene glycol) | 12% |
| Alcohol | 30% |
| Distilled Water | 57.80% |
| Perfume or Deodorant | 2% |

The above formulation can be used in the form of a spray which is advantageously non-toxic to animals to repel insect vermin from cats, dogs, cattle, etc., for example, after first shampooing to kill the existing insect population.

EXAMPLE V

Insecticide

| | |
|---|---|
| 5.5% Aloin stock solution | 10% |
| Quidewet Doss (surfactant) | 3% |
| Mineral Oil 85 USP | 43% |
| Kerosene | 42% |

| | |
|---|---|
| -continued | |
| Solvent* | 2% |

*Xylene, toluene, or benzene

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A method of killing invertebrate pests comprising exposing said pests to a compound selected from the group consisting of:

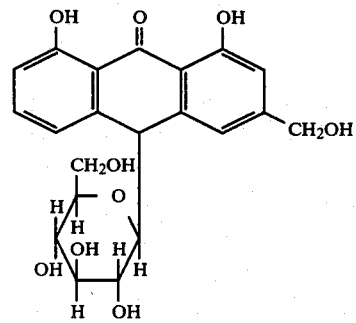

and

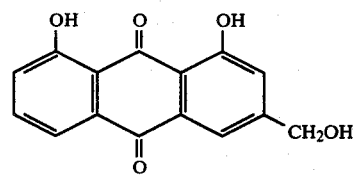

said compound being present in an amount sufficient to effect said killing.

2. The method of claim 1 wherein said compound is present in a composition comprising said compound and a carrier.

3. The method of claim 1 wherein said invertebrate pests are members of the phyla arthropoda and annelida.

4. The method of claim 2 wherein said composition further comprises at least one member selected from the group consisting of antioxidants, surfactants, perfumes, deodorants, and insect foods and attractants.

5. The method of claim 1, wherein said compound is present in a shampoo.

6. The method of claim 1, wherein said compound is applied to a host on which said pests are located.

7. The method of claim 6, wherein said host is a plant.

8. The method of claim 6, wherein said host is an animal.

9. The method of claim 6, further comprising the step of applying additional compound to said host after said killing has been effected to prevent reinfestation by said pests.

* * * * *